United States Patent [19]

Erhan

[11] Patent Number: 4,822,867

[45] Date of Patent: Apr. 18, 1989

[54] PROTEIN POLYMER GRAFTS

[76] Inventor: Semih Erhan, 2301 Cherry St., Apartment 12B, Philadelphia, Pa. 19103

[21] Appl. No.: 9,677

[22] Filed: Feb. 2, 1987

[51] Int. Cl.$^4$ ............................ C08H 1/00; C08H 1/02
[52] U.S. Cl. ..................................... 527/200; 527/201; 527/203; 527/206; 527/207
[58] Field of Search ............... 527/200, 201, 203, 206, 527/207

[56] References Cited

U.S. PATENT DOCUMENTS

| | | | |
|---|---|---|---|
| 2,183,929 | 12/1937 | Bowles et al. ................... | 527/207 |
| 2,264,732 | 12/1941 | Weber ............................. | 527/206 |
| 2,452,314 | 10/1946 | Morgan ........................... | 527/206 |
| 2,827,419 | 3/1958 | Tourtellote et al. ............. | 527/207 |
| 2,913,347 | 11/1959 | Pfirrmann ....................... | 527/207 |

FOREIGN PATENT DOCUMENTS

| | | | |
|---|---|---|---|
| 507965 | 12/1954 | Canada .......................... | 527/201 |
| 509913 | 10/1937 | United Kingdom ............. | 527/206 |

OTHER PUBLICATIONS

Kaleem et al., "Protein-Polymer Grafts, III A. Modification of Amino Acids I b. i Modification of Protein-Bound Arginine with 4-hydroxy Benzil", *J. of Biological Physics*, vol. 15, pp. 71–74, 1987.

*Primary Examiner*—John Kight
*Assistant Examiner*—Nathan M. Nutter
*Attorney, Agent, or Firm*—Steele, Gould & Fried

[57] ABSTRACT

A novel class of materials and processes used in their preparation are described. These materials are comprised of man-made polymers grafted onto protein backbone, specifically onto protein backbone, which has been selectively modified to be used as adhesives, coatings and construction materials. Man-made polymers can be selected from a group including condensation polymers such as phenolics, epoxides, polyamides, thiols, or addition polymers such as acrylics, vinyls and polyolefins. Grafting can be accomplished either stepwise or from already preformed polymers. Grafts can also be formed with more than one polymer either after the first graft is formed or simultaneously. Furthermore grafts can be formed onto a modified or unmodified protein whose backbone has been reduced to a polyamine.

6 Claims, No Drawings

PROTEIN POLYMER GRAFTS

BACKGROUND OF THE INVENTION

1. Field of Invention

This invention relates to the creation of a class of materials that do not exist in nature through grafting on man-made polymers onto protein backbone that combine the characteristics of both proteins and polymers. Proteins usually provide adhesion and the polymers the three dimensional crosslinking.

2. Description of the Prior Art

In the second half of the 20th Century, man-made polymers have become indispensable for daily life. From clothing to construction materials to binding metals together, they provide useful and sometimes indispendsable materials. However, they generally represent the end products of the petroleum industry, and in addition to being dependent on the fluctuations of that industry, they come from a source that is bound to run out. Proteins, on the other hand, have traditionally been considered primarily as food, and certain proteins such as collagen and casein were used as structural or paper adhesives. They have never been considered suitable as a source of high performance materials, even though, in the dry state, collagen has 10,000 p.s.i. tensile and over 3,000 p.s.i shear strength. This was basically due to moisture sensitivity of most proteins which resulted in protein bonds losing their mechanical properties and being attacked by microorganism. Compared with epoxide or phenolic resins, which have remarkable mechanical strength as well as moisture resistance, this shortcoming of proteins can be raced to the absence of three dimensional crosslinking. Certain proteins, on the other hand, such as barnacle cement and mussel adhesive, have the ability not only to set in the presence of water but also to be unaffected by it as well as by proteolytic enzymes. Barnacle cement can even bind to "Teflon". Available evidence shows clearly this resistance to be due to very tight three-dimensional crosslinking. It is easy to conclude, then, that if proteins could be modified appropriately so that they could be crosslinked with sufficient density, they, too, would be resistant to moisture as well as proteolytic degradation. They could then function as building blocks to high performance adhesives, coatings and structural materials.

There have been several attempts to graft acrylics, vinyls, etc. onto leather to improve its qualities, mostly moisture resistance and epoxides to develop new tanning methods but no attemps were made to specifically modify the backbone of a soluble protein to produce a new material.

Furthermore, in contradistinction to pertoleum based polymers, proteins represent a renewable resource.

SUMMARY OF THE INVENTION

The process briefly consists of the following steps:
I. Modification of the protein backbone
II. Grafting of the selected polymer
III. Curing on the graft

I.

A. Modification of the backbone entails modification of the following amino acids:
1. lysine: reductive alkylation, dinitrofluorobenzene reaction etc.
2. arginine: reaction with 4-hydroxybenzil, 4 hydroxyphenyl glyoxal, malonaldehyde derivatives, etc.
3. hydroxylated amino acids; serine, theonine, hydroxyproline: Williamson ether sythesis, conversion to amine through triphenyl phosphite dichloride, etc.
4. dicarboxylic acids: aspartic and glutamic acids: reaction with polyaziridines, chromium salts, zirconyl-and titanium salts, etc.
5. amidated amino acids; asparagine and glutamine.

B. These amino acids can be modified to carry:
1. phenolic,
2. amine,
3. sulfhydryl moieties
4. unsaturated moieties from the group comprised of vinyl, acrylic, etc. or their derivatives such as:
   i. phenyl ether
   ii. azide
   iii. sulfoxide, sulfone, etc.

II.

A. Grafting can involve group of polymers comprised of:
1. Epoxides
2. Phenolics
3. Heterocyclics
4. Polyamides
5. Sulfones
6. Acrylics, vinyl
7. Polyolefins
8. Polyurethanes, etc.

B. Grafts can be produced
1. Stepwise
2. From preformed polymer

C. Grafts can be prepared in cycles, i.e., after one graft is made the process is repeated to increase the branching and crosslinking density.

D. Grafts can be prepared directly onto the unmodified protein.

E. Grafts can be prepared onto modified or unmodified protein whose peptide backbone has been reduced to a polyamine.

III. Curing is effected using classical curing agents or their mixtures appropriate for each polymer grafted, such as polyamines, acid anhydrides, Lewis acids for epoxide formaldehyde or its derivatives such as hexa for phenolic grafts.

DESCRIPTION OF THE PROCEDURES USED IN THE INVENTION

The procedure of the present invention consists of a series of operations, generally as follows:

1. Protein is dissolved in buffer pH 4.5 to 10.0, with or without DMSO.
2. For the introduction of phenolic hydroxyls, phenolic aldehyde(s) are dissolved in DMSO or DMSO-buffer mixtures.
3. The reactant solutions are mixed together and a reducing agent such as sodium borohydride, sodium cyanoborohydride is added and the mixture is refluxed for 2-10 hours.
4. Unreacted reducing agent is destroyed by the addition of acids.
5. The product is isolated either through dialysis against buffer:DMSO mixture; gel filtration or precipitation by pouring into a solvent in which the protein is insoluble while the reactants are.

6. For epoxide grafts the isolated modified protein and sodium hydroxide are dissolved in water or equivalent amount of water and DMSO. Epichlorohydrin dissolved in an appropriate solvent is added dropwise with stirring. The mixture is refluxed for 3-8 hours.

7. The product is isolated by dialysis, gel filtration of precipitation with an appropriate solvent.

8. The epoxidized protein is dissolved in an appropriate solvent, such as DMSO, in a three-necked flask equipped with a reflux condenser and heated to 50°-100° C. Appropriate molar excess of polyfunctional phenol, neat or dissolved in a solvent, is added, followed by sodium hydroxide added in small portions. The reaction is run for 5-10 hours.

9. The product is isolated by dialysis, gel filtration, precipitation with an appropriate solvent or a combination of these processes.

10. The product is dissolved in water and epoxidized as under 6 through 7.

11. The curing is effected using specific procedures appropriate for each grafted polymer as described further down.

DESCRIPTION OF THE PREFERRED EMBODIMENTS OF THE INVENTION

I. A.1. Modification of lysines a. Reductive alkylation: 5 g gelatin corresponding to 200 mg of lysine (1.408 mM) was dissolved in 70 ml borax buffer (pH 7.2). Ten molar excess of phenolic aldehyde and 10 molar excess of sodium cyanoborohydride were dissolved in 70 ml of DMSO and were added to gelatin solution, dropwise, under constant stirring for five hours, the mixture was acidified with 6NHCl to destroy unreacted cyanoborohydride and was precipitated by pouring into acetone. The precipitate was washed several times with acetone and either was dialyzed against 0.006N acid or passed over Bio-Gel P-2 column to remove unreacted low molecular reagent traces.

b. Introduction of $-NO_2$ and $-NH_2$ groups: Protein is treated with dinitrofluorobenzene in appropriate solvents. $-NH_2$ groups are obtained after the modified protein in treated with appropriate reducing agents: electrochemical reduction, $SnCl_2+HCl$, sulfuretted sodium borohydride, sodium hydrosulfite, etc. I. A.2. Modification of arginines a. Reaction with 4-hydroxybenzil: 2.0 g gelatin and 2.0 g of sodium hydroxide (or an equivalent amount of potassium hydroxide) were dissolved in 50 ml distilled water. To this solution containing 178 mg of bound arginine (1.022 m moles) 2.14 g benzil or 2.305 g 4-hydroxybenzil dissolved in 100 ml of ethanol (95%) was added, Nitrogen was bubbled through the solution for 30 minutes and the flask was covered with a stopper. The mixture was allowed to stand overnight (16-18 hours) with constant stirring. The solution was neutralized with concentrated hydrochloric acid and ethanol was removed under vacuum at 40° C. During this step, unreacted benzil or hydroxybenzil precipitated out and was removed by filtration. Modified gelatin was dialyzed against 0.001 N acetic acid for 24 hours with several changes to remove low molecular reactants. Purity of the product was checked by passing an aliquot on Bio-Gel P-2 column, equilibrated with borax buffer pH 7.2. Modified gelatin was eluted and lyophilized as a single peak. To establish the extent of modification, Sakaguchi test was applied. 0.5 g of lyophilized product was dissolved in water (50 ml) and passed through Bio-Gel P-2 column equilibrated with 1N ammonium hydroxide. Sakaguchi reaction showed 100% modification with benzil and 96% with 4-hydroxybenzil.

I. A.3. Modification of hydroxylated amino acids
  Serine, Threonine, Hydroxyproline
  Two different reactions are used:

a. Conversion of hydroxylated amino acids (R—OH) into an amino acidhalide (R—X) followed by conversion into an amine (R—$NH_2$), b. Conversion of hydroxylated amino acids into an ether
  (R—O—R)

a. Conversion of hydroxylated amino acids into alkylhalide:

i. tri-n-octylphosphine-$CCl_4$ reaction:

Gelatin, corresponding to 10 m mole hydroxylated amino acids is dissolved in DMSO, and 20 ml $CCl_4$ is added. The reaction mixture is cooled in an ice bath and 10.5 m moles tri-n-octylphospin is added during several minutes. After 5 minutes the reaction mixture is poured into excess acetone, filtered and washed with fresh acetone.

ii. Reaction with triphenylphosphitedihalides:

This reaction is especially attractive because the reaction product (pHO) $POX_2$ does not react with the alcohol further under the prevailing conditions.

Preparing of triphenylphosphitedichloride:

Dry $Cl_2$ is passed through triphenylphosphite with cooling and stirring under strict exclusion of moisture, until equivalent weight is taken up. All crude dihalides are suitable for reaction with alcohols without further purification.

This reaction, too, is applicable to secondary and tertiary alcohol and threonine and hydroxyproline can be expected to reacts, also.

Gelatin, corresponding to 10 m mole hydroxylated amino acids, dissolved in DMSO is added dropwise into 11 m mole crude triphenylphosphitedichloride, at room temperature and the reaction is completed with gentle warming. The product is isolated by pouring into acetone which precipitates the protein. It is filtered and washed with acetone.

iii. Conversion of halides into amines:

The modified gelatin is dissolved in water and treated with 1.1 molar excess of hexamethylenetetramine (hexa) in a flask equipped with a reflux condenser. To ensure complete solution of hexa sufficient solvent is taken and the mixture is refluxed for 24 hours. After cooling the mixture is poured into acetone to isolate the hexasalt of the protein. The salt then is dissolved in 2N ethanolic HCl and after several hours the ethanol is removed by distillation leaving the amine modified gelatin.

b. Conversion of serine into an ether (Williamson Synthesis):

Due to its enhanced chemical stability ethers are attractive in application where exposure to severe conditions are expected. Aryl ethers are still better in this respect.

p-aminophenol is dissolved in equivalent amount of NaOH solution 10 m mole aminophenol containing reaction mixture is reacted with gelatin, dissolved in DMSO: water =50:50, whose hydroxylated amino acids have been converted to halide derivative, according to classical Williamson reaction.

2. Modification as asparagine and glutamine:

These amino acids are reduced directly to amines with $LiAlH_4$. All reactions are to be carried out in the three-necked flask equipped with stirrer, dropping funnel, reflux condensor and a thermometer.

Gelatine corresponding to 0.2 mole of asparagine and glutamine is dissolved in 300 ml of dry DMSO and added, dropwise, into the flask containing 0.25 moles of LiAlH$_4$ in 250 ml dry DMSO. After overnight stay the excess LiAlH$_4$ is decomposed with HCL and the neutralized solution is poured into acetone to precipitate the modified protein. It is filtered and washed with acetone.

The extent of modification is determined by amino acid composition determination after acid hydrolysis. Needless to say, the extent of modification of other amino acids, too, is established through amino acid analyses.

3. Modification of aspartic and glutamic acids:

Propriety polyaziridines called XAMA-2 and 7, obtained from Cordoba Chemical Company, are used during curing, which reacts with free carboxyl groups and thus obviates the need to modify these amino acids, a simple method to achieve this goal if needed is to convert to free caboxyl groups to methyl esters using dimethylsulfate or diazomethane and reduce the amides as described under 2.

Grafting:

A. Epoxide Grafts 3 g of 50% modified protein, 0.2 g of sodium hydroxide were dissolved in 25 ml distilled water. 2 ml epichlorohydrin was dissolved in 5 ml of DMSO, in a three necked flask equipped with a dropping funnel and condenser. The flask was heated to 60° C. and the protein solution was added, dropwise over 15 minutes with constant stirring. After 5 hours the mixture was poured into excess acetone, filtered, washed and dried in vacuo.

8 g of epoxidized protein was dissolved in 50 ml DMSO in a three necked flask, equipped with a condenser and a dropping funnel. The solution was heated to 50° C. and a 5 molar excess of bispheonol-A was added. After dissolution equimolar amount of sodium hydroxide was added, dropwise, as a 40% aqueous solution. The reaction was run for six hours and the produce was obtained by pouring into excess acetone. The precipitate was filtered and washed with acetone several times. To remove the precipitated sodium hydroxide the product was dissolved in pH 7.2 borax buffer and passed over Biogel P-2 column. The product, which elutes within the void volume, was obtained by precipitation with acetone.

The product was dissolved is distilled water and subject to epoxidation exactly as discussed under 2.

B. Resorcinol-formaldehyde grafts

A 2% solution of modified gelatin in DMSO is treated with 50 molar excess of formaldehyde, which was added dropwise over a period of 30 minutes. pH is adjusted to 10 with 40% aqueous sodium hydroxide and the mixture is heated for 5 hours at 90° C. The reaction product is precipitated by pouring into excess acetone or methanol. The product is washed extensively with the same solvent (Product 1).

1 g of dry Product I and 2.72 g resorcinol are dissolved in DMSO and the pH of the medium was made 11–12 by the addition of 40% aqueous sodium hydroxide. Reaction mixture is heated at 70° C. for 30 minutes and 90° C. 12 for 4½ hours. The products are isolated by pouring into acetone. It is dried in vacuum dessicator overnight, at room temperature.

Curing:

Dry adhesive is mixed with a proprietary polyaziridine XAMA-2 (obtained from Cordoba Chemical Co., N. Muskegon, MI) into a homogeneous slurry and tetra aminobenzene, pyromellitic anhydride etc. is added and the mixture is cured at 150° C. for four hours and allowed to cool slowly to room temperature.

Selective Examples of Applications

Metal binding adhesives:

Gelatin-epoxide grafts bind metals, plastics, etc. A graft having 10% crosslinking density binds aluminum coupons, prepared according to Forest Products Laboratory method, with a tensile strength of ca. 4,000 p.s.i. Stainless steel coupons, which have been prepared with sandblasting, exhibit a tensile strength of 1,500 p.s.i.

Thermoset resins A gelatin-resorcinol-formaldehyde graft having 10% crosslinking density exhibits thermosetting characteristics. It can be shaped, after incorporation of appropriate fillers, into three-dimensional structures.

Flexibilized protein

Polyglycerin containing 3 to 10 molecules of glycerin is epoxidized with epichlorohydrin in strong alkali. Normal or modified gelatin is treated with epoxidized polyglycerin under standard conditions. The product is isolated as described above by pouring into acetone. The material can be cast into films of different thickness which can be used as artificial skin/wound cover or as industrial coating.

The product can also be mixed with crosslinking agents such as polyaziridines, chromium, zirconyl or titanium salts and formed into shapes and cured under heat and/or pressure to obtain permanently flexibilized objects. A ball made from such a material bounces, a circle remembers its original shape after being stretched.

What is claimed is:

1. A process for modifying protein-bound arginine which comprises reacting an arginine containing gelatin with a compound selected from the group consisting of benzil and 4-hydroxybenzil in a suitable solvent in the presence of a base.

2. The process of claim 1 wherein said compound is 4-hydroxybenzil.

3. The process of claim 1 wherein said compound is benzil.

4. The reaction product of the process of claim 1.

5. The reaction product of the process of claim 2.

6. The reaction product of the process of claim 3.

* * * * *

UNITED STATES PATENT AND TRADEMARK OFFICE
CERTIFICATE OF CORRECTION

PATENT NO.  : 4,822,867
DATED       : April 18, 1989
INVENTOR(S) : Semih Erhan

It is certified that error appears in the above-identified patent and that said Letters Patent is hereby corrected as shown below:

In Column 1, line 7, change "on" to --of--.

In Column 1, line 34, change "raced" to --traced--.

In Column 1, line 62, change "on" to --of--.

In Column 2, line 4, change "theonine" to --threonine--.

In Column 3, line 45, move "I. A.2" to Column 3, line 46 before "Modification".
In Column 4, line 35, change "reacts" to --react--.

Signed and Sealed this

Twenty-fourth Day of April, 1990

*Attest:*

HARRY F. MANBECK, JR.

*Attesting Officer*      *Commissioner of Patents and Trademarks*